United States Patent [19]

Koski

[11] Patent Number: 4,657,034

[45] Date of Patent: Apr. 14, 1987

[54] DENTAL FLOSS DISPENSER

[76] Inventor: Philip A. Koski, 7588 Groveland Rd., Minneapolis, Minn. 55432

[21] Appl. No.: 920,217

[22] Filed: Oct. 17, 1986

[51] Int. Cl.⁴ ............................................. A61C 15/00
[52] U.S. Cl. ................... 132/92 R; 132/92 A; 132/91
[58] Field of Search ...................... 132/91, 92 R, 92 A

[56] References Cited

U.S. PATENT DOCUMENTS

| | | | |
|---|---|---|---|
| 465,677 | 12/1891 | Pettit | 132/92 R |
| 1,608,212 | 11/1926 | Hochstadter | 132/92 R |
| 2,384,712 | 9/1945 | Turenchalk et al. | 132/91 |
| 2,460,591 | 2/1949 | Luzar | 132/92 R |
| 2,853,082 | 9/1958 | Nelson | 132/92 R |
| 3,863,655 | 2/1975 | Smith | 132/91 |
| 3,870,059 | 3/1975 | Bennington | 132/92 A |
| 3,881,502 | 5/1975 | Bennington | 132/91 |
| 3,885,579 | 5/1975 | Navrat | 132/92 R |
| 4,206,774 | 6/1980 | Griparis | 132/92 R |
| 4,232,688 | 11/1980 | Day | 132/91 |
| 4,434,807 | 3/1984 | Huskey | 132/92 A |
| 4,495,957 | 1/1985 | Beggs et al. | 132/92 A |
| 4,518,000 | 5/1985 | Leverette | 132/92 A |
| 4,522,216 | 6/1985 | Bunker | 132/92 R |

Primary Examiner—John J. Wilson
Attorney, Agent, or Firm—George Leone

[57] ABSTRACT

A dental floss dispenser comprising a container, a feed through tube, a twist-and-lock mechanism, and a barrel. The container is adapted to hold a reel of dental floss which is connected to a barrel. A tube is inserted into the barrel and dental floss is fed through the tube emerging at a feed through hole in a second end. The tube has a flared end cap which extends beyond the barrel tip. A twist-open-and-lock mechanism causes the flared end cap to behave in a reciprocating manner with respect to the barrel tip thereby alternately freeing and pinching the floss against the barrel tip.

8 Claims, 4 Drawing Figures

DENTAL FLOSS DISPENSER

BACKGROUND OF THE INVENTION

1. Field of the invention

The present invention relates to dental floss dispensers and more particularly to dental floss dispensers which minimize the need for insertion of fingers into the mouth of the user.

2. Description of the Prior art

There have been many previous attempts at designing a dental floss dispenser which would be easy to use and minimize the necessity for inserting the hands of the user into the mouth. Many of these inventions, such as the one found in U.S. Pat. Nos. 3,870,059 to Bennington involve brake means which are used to control the floss during use and withdrawing thereof. However, such devices usually require the insertion of fingers into the mouth and do not provide a positive, easy to use method of keeping the floss at high tension.

An object of this invention is to provide a dental floss dispenser having ease of handling and use without the need for inserting the hands or fingers of the user into the mouth.

A further object of this invention is to provide a dental floss dispenser which has an easy to use, and reliable tensioning mechanism.

A feature of the invention is that, when the floss is locked in place, saliva and water are effectively sealed out of the interior of the barrel of the dispenser.

These and other features and advantages of the invention will appear from the following detailed description of the specific embodiments thereof taken in connection with the drawings below.

SUMMARY

A dental floss dispenser is disclosed comprising: a container having first and second ends adapted to hold a reel of dental floss; a barrel including a barrel tip; a tube having first and second ends, the tube being inserted in the barrel and having an interior diameter large enough such that a line of dental floss could be fed through the tube and further having a flared end cap at its second end extending beyond the barrel tip and a floss exit hole located between the flared end cap and the first end of the tube; and means for twisting open and locking the floss comprising a female connector having first and second ends wherein the first end is rigidly attached to the barrel and the second end forms a cylinder which has a threaded interior, a male connector having first and second ends wherein its first end is threaded and adapted to mate with the second end of the female connector and its second end has a hole and is attached to the first end of the tube. The twist-and-lock means additionally comprises a sleeve which is rotatably clamped to the second end of the female connector and partially encases the female connector. The sleeve is of a sufficient interior diameter to allow the male connector to freely reciprocate within the sleeve, and the sleeve is rigidly connected to the interior wall of the container such that a twist of the container in a first direction in relation to the barrel will allow the line of floss to be pulled out through the floss exit hole and a twist of the container in a second direction will lock the floss in place, pinching it between the flared end cap and the barrel tip.

BRIEF DESCRIPTION OF THE DRAWINGS

For a more complete understanding of the invention, reference is hereby made to the drawings in which.

DESCRIPTION OF THE PREFERRED EMBODIMENT

Figure 1:
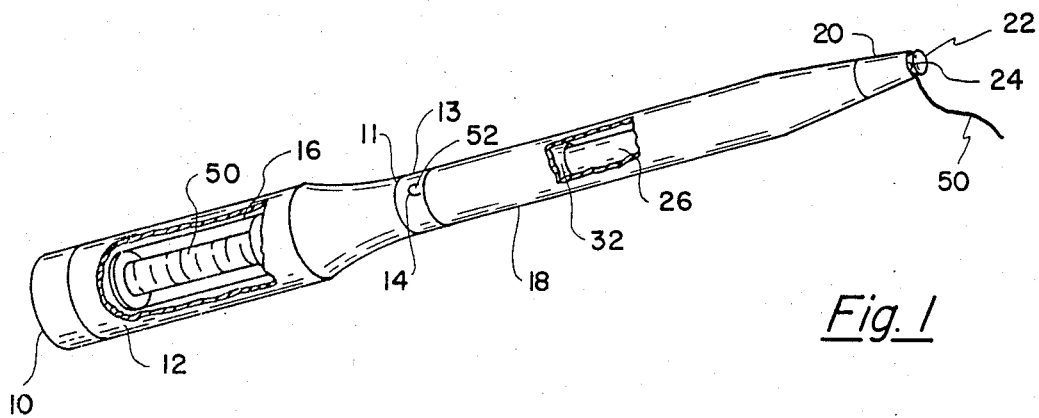
FIG. 1 is one embodiment of the dental floss dispenser of the invention.

FIG. 1 shows one embodiment of the dental floss dispenser of the invention. The dental floss dispenser comprises a container 12, a removable cap 10, a cutting edge 14, a barrel 18, a tip 20, a flared end cap 22, a floss exit hole 24, a feed tube 26, and a twist-open-and-lock means 32 (shown in detail in FIG. 3). The container 12 is adapted to hold a reel of dental floss 50 further contained in the floss holding means (shown in detail in FIG. 2). The barrel 18 engages one end of the twist-and-lock means 32 as described below and includes a tip 20. A removable cap 10 is preferably attached to the first end of the container 12. Those skilled in the art will recognize that the dental floss dispenser of the invention may be manufactured with a permanent cap if a disposable dispenser is desired. The use of a removable cap 10 is preferable if one desires to have a reuseable unit wherein the dental floss holding means 16 may be replaced as the floss in the holding means is depleted. Similarly, while the cutting edge 14 is a desirable feature, it is not necessary for the operation of the present invention. In one embodiment of the invention, the cutting edge 14 was punched out of band 13 and attached to barrel 18. One may advantageously eliminate band 13 and punch the cutting edge out of the material comprising barrel 18 or container 12.

The tube 26 is inserted in the barrel 18 and has an interior diameter large enough such that a line of dental floss 50 can be fed through the tube. The tube further has a flared end cap 22 extending beyond the barrel tip 20. A floss exit hole 24 is located in the tube 26 between the flared end cap 22 and the second end of the tube. Means for twisting open and locking the floss 32 to attain sufficient tension to allow flossing of the teeth is attached to the tube 26, to the container 12 and to the barrel 18 as described in detail below.

Figure 2:
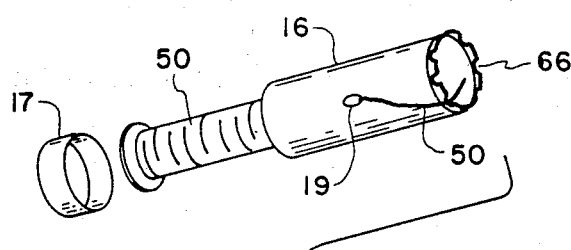
FIG. 2 is a detailed drawing of the floss holding means having a feed through hole.

Referring now to FIG. 2, a more detailed drawing of the floss holding means 16 is shown. A reel of floss 50 is contained within the floss holding means 16 as shown. The floss holding means 16 may be a cylindrical container with a cap 17 at one end which allows the replacement of the floss reel when the supply of floss is depleted. A collar 66 extends outwardly away from the other end of holding means 16. At least one notch may advantageously be cut into collar 66 to aid in guiding the floss as it feeds into tube 26. A first feed through hole 19 is located advantageously at one end of the floss holding means 16, although the placement of the feed through hole is not critical.

Figure 3:
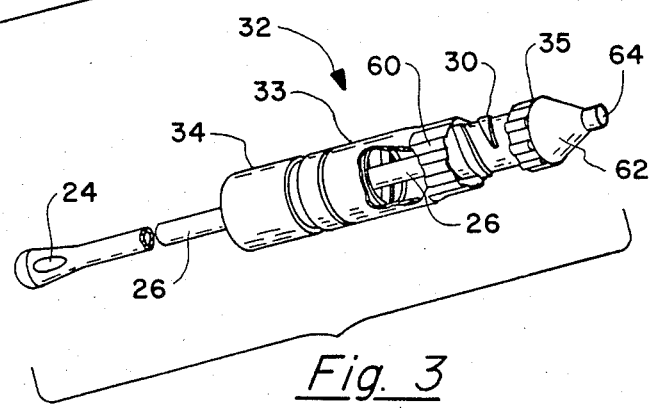
FIG. 3 is a detailed drawing of the twist-and-lock means.

Referring now to FIG. 3, a detailed drawing of the twist-and-lock means 32 is shown. The twist-and-lock means 32 comprises a female connector 34 mated to a male connector 30 which is also attached to feed tube 26. The twist-and-lock means 32 is advantageously partially encased in a sleeve 33 which is, in turn, press fit into or otherwise rigidly attached to container 12 at end 11 (shown in FIG. 1). Sleeve 33 advantageously has grooves 60 which facilitate the press fit into end 11. Sleeve 33 is clamped around a groove 60 on female connector 34 such that female connector 34 slidably rotates within sleeve 33. Sleeve 33 is of a diameter suitably larger than male connector 30 to allow male connector 30 to freely reciprocate inside of sleeve 33. The female connector 34 is advantageously a cylindrical sleeve with a first and second end. The first end is threaded so as to form a female threaded connection suitable to accept the male connector 30 which is threaded at a first end in a manner adapted to mate with the female connector such that a twist in one direction, for example, counterclockwise, will push the male connector 30 outwardly away from the female connector. Conversely turning the female or male connector in the other direction causes the male connector 30 to be screwed inwardly into the female connector 34. The feed tube 26 is rigidly attached to the second end 35 of the male connector using standard fastening techniques. In one embodiment of the invention an epoxy 62 was used to fasten tube 26 to the second end 35 of connector 30. The second end 35 may alternatively be a cap having a hole 64 which is then aligned with and attached to feed tube 26 by standard fastening techniques. The second end of female connector 34 extends outside of the sleeve 33 and is rigidly attached by means of a press fit or other well known attachment means to one end of barrel 18. In operation, therefore, when barrel 18 is twisted in relation to container 12, female connector 34 turns with barrel 18 thereby allowing male connector 30 to reciprocate within sleeve 33. As the male connector 30 reciprocates inwardly or outwardly as a result of the twisting or rotation of the female connector 34, the cap 22 of the tube 26 correspondingly advances inwardly toward the barrel tip 20 or outwardly away from the barrel tip 20 thereby alternately freeing or locking the floss 50 away from or against the barrel tip. One can see with reference to FIG. 1 that when the male connector 30 is screwed outwardly away from the female connector, the cap is forced against the tip 20 of the barrel 26—pinching and locking the line of floss 50 against the barrel tip 20.

Figure 4:
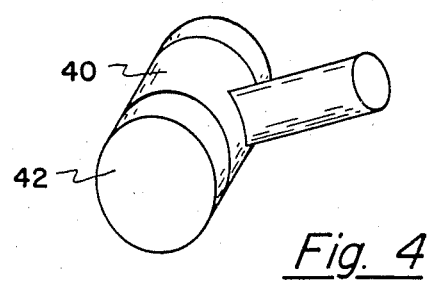
FIG. 4 is a drawing of an alternate embodiment of the floss holding means of the present invention.

FIG. 4 shows an alternate embodiment of the floss holding means of the present invention wherein the container 12 has been replaced by an alternate form of container 40. The container 40 has an end cap 42 which may be removed to allow the insertion of a standard reel of dental floss such that the axis of the reel is perpendicular to the axis of the barrel. The floss is then fed through the feed through tube 26. This assembly would then be connected to the remaining device in place of container 12. This embodiment of the invention would allow the use of many standard types of reels of floss which are presently available. It also does not require the use of a second container such as floss holding means 16, but the standard reel may be used without adaptation.

In general, one uses the dental floss dispenser of the present invention by twisting open the dispenser to free the string of floss at the tip 20 and pulling out a desired length of floss 50. Next the dispenser is twisted closed, pinching the length of floss tight against the tip 20. The loose end of the floss is wrapped around the finger of one hand to leave a convenient length between the finger and the dispenser, suitable for cleaning teeth. The dispenser may be inserted into the mouth during flossing without the need for also inserting a finger.

While there has been shown and described a preferred embodiment of the invention, those skilled in the art will appreciate that various changes and modifications may be made to the illustrated embodiment without departing from the true spirit and scope of the invention which is to be determined from the appended claims.

What is claimed is:

1. A dental floss dispenser comprising:
   A. a container having first and second ends adapted to hold a reel of dental floss;
   B. a barrel including a barrel tip;
   C. a tube having first and second ends, the tube being inserted in the barrel and having an interior diameter large enough such that a line of dental floss could be fed through the tube and further having a flared end cap at its second end extending beyond the barrel tip and a floss exit hole located between the flared end cap and the first end of the tube; and
   D. means for twisting open and locking the floss comprising a female connector having first and second ends wherein the first end is rigidly attached to the barrel and the second end forms a cylinder which has a threaded interior, a male connector having first and second ends wherein its first end is threaded and adapted to mate with the second end of the female connector and its second end has a hole and is attached to the first end of the tube, and wherein the twist-and-lock means additionally comprises a sleeve which is rotatably clamped to the second end of the female connector and partially encases the female connector, wherein the sleeve is of a sufficient interior diameter to allow the male connector to freely reciprocate within the sleeve, and wherein the sleeve is rigidly connected to the interior wall of the container such that a twist of the container in a first direction in relation to the barrel will allow the line of floss to be pulled out through the floss exit hole and a twist of the container in a second direction will lock the floss in place, pinching it between the flared end cap and the barrel tip.

2. The apparatus of claim 1 wherein the container additionally includes a removable cap to allow replacement of the dental floss reel.

3. The apparatus of claim 2 wherein the barrel additionally includes a floss cutting edge.

4. The apparatus of claim 3 wherein the floss cutting edge is located on the outer wall of the barrel.

5. The apparatus of claim 4 wherein the container is adapted to contain floss holding means.

6. The apparatus of claim 5 wherein the floss holding means comprises a cylinder having first and second ends wherein the second end further comprises a collar having at least one notch, the cylinder being suitable to contain a reel of floss and further having a feed through hole for the floss.

7. The apparatus of claim 6 wherein the first end of the floss holding means comprises a removable cap.

8. The apparatus of claim 1 wherein the container comprises a cylinder wherein a reel of floss is contained such that the axis of the reel is perpendicular to the axis of the barrel.

* * * * *